(12) United States Patent
Saunders et al.

(10) Patent No.: US 8,277,405 B2
(45) Date of Patent: Oct. 2, 2012

(54) POST-COITAL FEMININE HYGIENE DEVICE

(76) Inventors: Anntoinette Saunders, Mechanicsburg, PA (US); Devon Saunders, Mechanicsburg, PA (US)

( * ) Notice: Subject to any disclaimer, the term of this patent is extended or adjusted under 35 U.S.C. 154(b) by 729 days.

(21) Appl. No.: 11/845,574

(22) Filed: Aug. 27, 2007

(65) Prior Publication Data

US 2009/0062715 A1     Mar. 5, 2009

(51) Int. Cl.
*A61M 35/00*     (2006.01)

(52) U.S. Cl. ................ 604/1; 604/30; 601/154

(58) Field of Classification Search .......... 604/11, 604/358, 385.17, 385.18, 1–3, 27, 30, 36, 604/47; 601/154
See application file for complete search history.

(56) References Cited

U.S. PATENT DOCUMENTS

| | | | | |
|---|---|---|---|---|
| 3,228,398 | A | * | 1/1966 | Leonard et al. ............ 604/1 |
| 5,692,261 | A | | 12/1997 | Lops |
| 2006/0069338 | A1 | * | 3/2006 | Bichsel et al. ............ 604/2 |
| 2006/0137434 | A1 | * | 6/2006 | Cohen et al. ............ 73/61.43 |

FOREIGN PATENT DOCUMENTS

GB     2278543 A   *   12/1994

\* cited by examiner

*Primary Examiner* — Melanie Hand

(57) ABSTRACT

A feminine hygiene device to wipe seminal and other fluids from the vagina after sexual intercourse.

6 Claims, 3 Drawing Sheets

POST-COITAL FEMININE HYGIENE DEVICE

BACKGROUND

1. Field of the Invention

The present disclosure relates to the field of feminine hygiene, particularly that after sexual intercourse.

2. Background

After sexual intercourse without a condom, a woman likely has seminal fluid present in her vagina. If she then stands or moves about in an upright position, this fluid can drain out of her vagina. This can present a problem in that the fluid can soil her clothing or generally make her feel uncomfortable.

Several methods for dealing with this problem presently exist, but all have shortcomings. First, a woman can simply wait for the fluid to drain out or be absorbed, but this can be time consuming and uncomfortable.

A woman could attempt to accelerate the process by wiping her exterior genitalia to help to absorb some of the fluid as it drains out, but the draining process can still take an extended period of time and continual wiping can be a nuisance. A panty liner may be worn to absorb the fluid and protect clothing without as much need for wiping. However, this can also be uncomfortable and inconvenient.

What is needed is a device to efficiently and effectively remove seminal and other fluids from the vagina after sexual intercourse.

DETAILED DESCRIPTION

Figure 1:
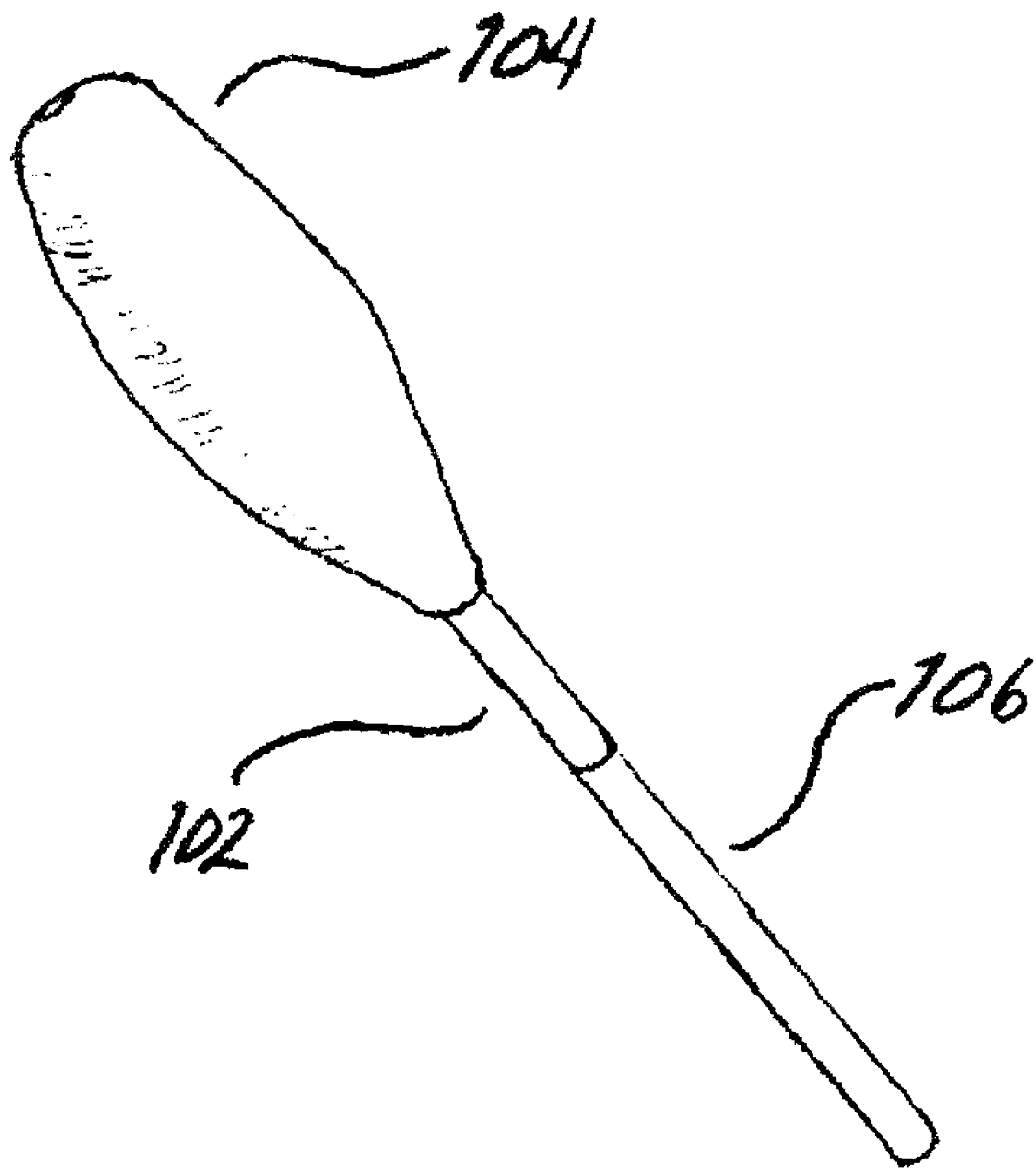
FIG. 1 depicts a perspective view of an embodiment of the present device.

FIG. 1 depicts a perspective view of one embodiment of the present device. A central elongated member 102 can have an absorbent member 104 covering at least the distal portion of said central elongated member 102. In some embodiments, as shown in FIG. 1a, the distal end of a second elongated member 106 can be removably connected with the proximal end of said central elongated member 102.

Figure 1A:
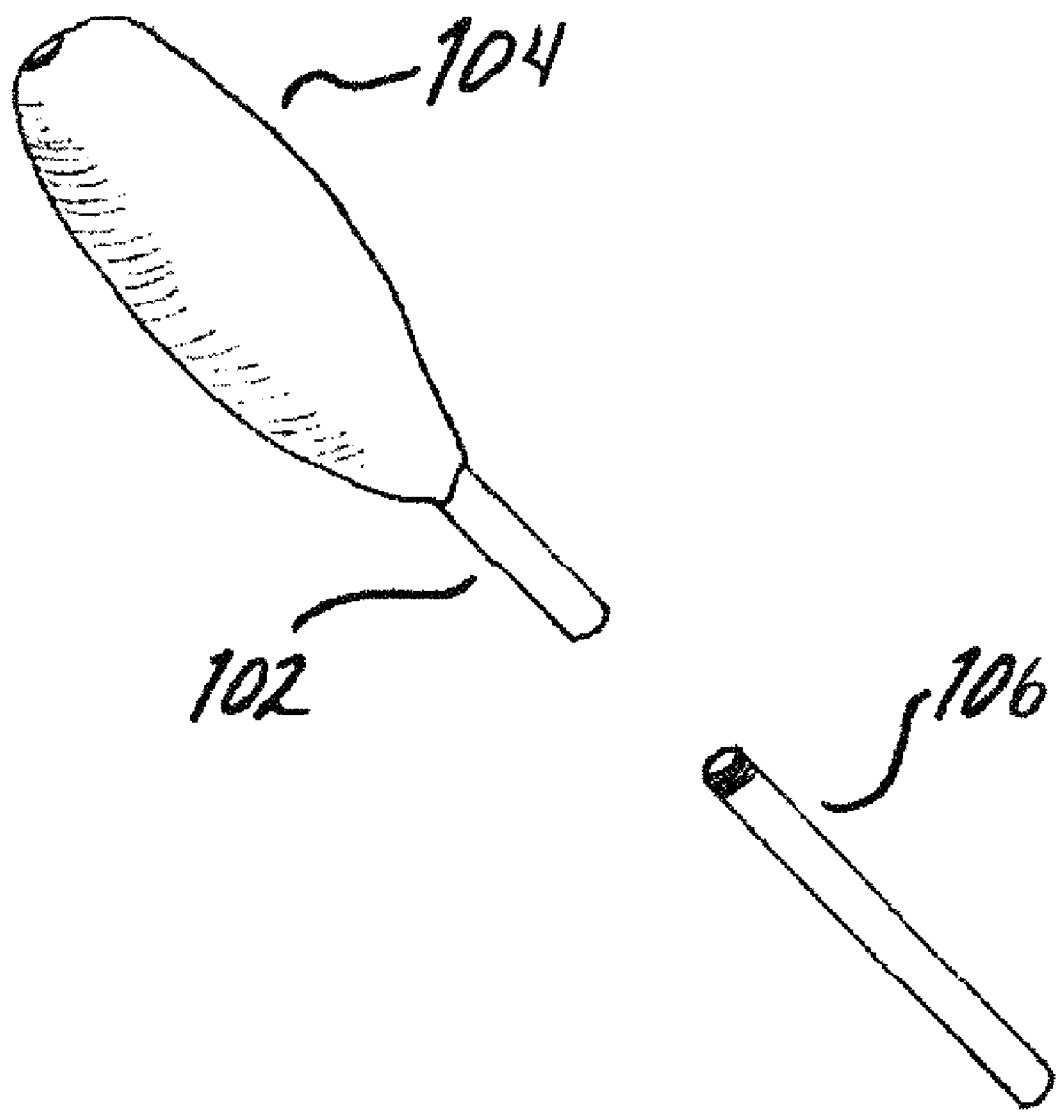
FIG. 1a depicts a detail of an embodiment of the present device.

In some embodiments, a second elongated member 106 can be removably connected to said central elongated member 102 via a threaded connection, as shown in FIG. 1a. However, in other embodiments, the second elongated member 106 can be removably connected to said central elongated member 102 by a snap-fit, friction-fit, adhesive, or any other known and/or convenient device. Further, in some embodiments, said second elongated member 106 can be hollow, but in other embodiments can be solid or partially hollow. In some embodiments, said second elongated member 106 can have a circular cross-section, but in other embodiments can have any known or convenient cross-section. In some embodiments, said second elongated member 106 can be made of a polymer, but in other embodiments, can be made of a paper product, biodegradable material, or any other known and/or convenient material.

Figure 1B:
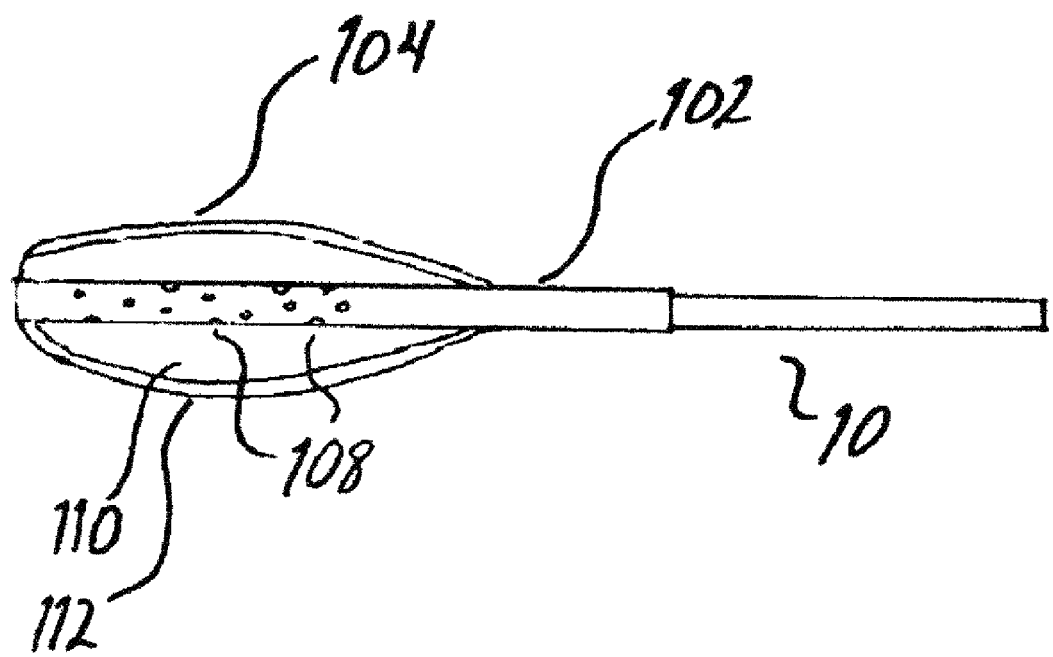
FIG. 1b depicts a detail of a longitudinal cross-section of an embodiment of the present device.

In some embodiments, as shown in FIG. 1b, at least the distal portion of a central elongated member 102 can be hollow. A plurality of openings 108 can be cut into the walls of at least the hollow portion of a central elongated member 102. In other embodiments, the entire central elongated member 102 can be hollow, with a plurality of openings 108 cut into the walls along the entire length, or only along the distal portion of a central elongated member 102. In some embodiments, a central elongated member 102 can have a circular cross-section, but in other embodiments can have any known or convenient cross-section. In some embodiments, aid central elongated member 102 can be made of a polymer, but in other embodiments can be made of a paper product, biodegradable material, or any other known and/or convenient material.

In some embodiments, an absorbent member 104 can surround at least the distal portion of a central elongated member 102. Although an absorbent material can be comprised of a single material, in some embodiments, an absorbent member 104 can have a multi-layered construction comprising at least one layer of absorbent material 110 surrounded by at least one layer of wicking material 112. Said at least one layer of wicking material 112 can also have textural characteristics to enhance the wiping efficacy of the present device. At least one layer of absorbent material 110 can be made of cotton or any other known and/or convenient natural or synthetic material. At least one layer of wicking material 112 can be made of any known and/or convenient material that has wicking properties.

In some embodiments, as shown in FIG. 1b, an absorbent member 104 can cover the sides of at least the distal portion of a hollow central elongated member 102, leaving the distal end of a hollow central elongated member 102, open to the exterior surface of an absorbent member 104. However, in other embodiments, an absorbent member can cover the distal end of a central elongated member 102.

In use, the distal end of the present device can be inserted into the vagina following sexual intercourse. A user can move the present device in a sweeping and/or rotational motion such that the absorbent member 104 can wipe seminal fluids from the vaginal walls. In some embodiments having a hollow central member 102 in which the distal end is open to the outer surface of the absorbent member 104, the seminal fluid can be channeled into the distal opening of the hollow central member 102. Further, in embodiments in which the walls of at least the distal portion of a hollow central elongated member 102 are perforated, a plurality of openings 108 can also channel seminal fluid that has entered an absorbent member 104 into the interior of a hollow central elongated member 102. At least one layer of wicking material 112 can help to remove the seminal fluid from the vaginal walls and then pull the fluid in towards the at least one layer of absorbent material 110. A plurality of holes 108 in a hollow central elongated member 102 can further improve the absorption capabilities of the present device. In some embodiments, a second elongated member 106 can provide additional length to facilitate insertion into the vagina.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. A feminine hygiene device comprising:

a central elongated member having a proximal end and a proximal portion and a distal end and a distal portion;

at least one layer of absorbent material, having an outer surface and an inner surface, proximal to and surrounding the outer surface of said distal portion of said central elongated member;

at least one layer of wicking material substantially covering and external to the outer surface of said at least one layer of absorbent material.

2. The device of claim 1, further comprising an elongated member having a proximal end and a distal end that is removably connected to the proximal end of said central elongated member.

3. The device of claim 1, wherein at least the distal portion of said elongated central member is hollow.

4. The device of claim 3, wherein at least the distal portion of the walls of said hollow elongated central member are perforated.

5. The device of claim 4, wherein the distal end of said elongated central member is open to the outer surface of said absorbent member.

6. The device of claim 5, further comprising an elongated member having a proximal end and a distal end that is removably connected to the proximal end of said central elongated member.

* * * * *